(12) United States Patent
Rieker

(10) Patent No.: US 11,703,188 B2
(45) Date of Patent: Jul. 18, 2023

(54) GAS CYLINDER MONITORING SYSTEM

(71) Applicant: Linde Aktiengesellschaft, Munich (DE)

(72) Inventor: Bernd Rieker, Landsberg (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 845 days.

(21) Appl. No.: 16/623,465

(22) PCT Filed: Jun. 19, 2018

(86) PCT No.: PCT/EP2018/066165
§ 371 (c)(1),
(2) Date: Dec. 17, 2019

(87) PCT Pub. No.: WO2018/234263
PCT Pub. Date: Dec. 27, 2018

(65) Prior Publication Data
US 2020/0182411 A1 Jun. 11, 2020

(30) Foreign Application Priority Data
Jun. 19, 2017 (GB) .................................. 1709702

(51) Int. Cl.
*F17C 13/02* (2006.01)
*F17C 13/04* (2006.01)
(Continued)

(52) U.S. Cl.
CPC ............... *F17C 13/02* (2013.01); *F17C 13/04* (2013.01); *F17C 13/06* (2013.01);
(Continued)

(58) Field of Classification Search
CPC .......... F17C 13/02; F17C 13/04; F17C 13/06; F17C 2201/0109; F17C 2201/054;
(Continued)

(56) References Cited

U.S. PATENT DOCUMENTS

2002/0070236 A1* 6/2002 Wolf .................. B65D 41/3419
222/153.05
2004/0045608 A1 3/2004 Peters et al.
(Continued)

FOREIGN PATENT DOCUMENTS

EP 1 356 228 B1 8/2008

OTHER PUBLICATIONS

International Search Report of the International Searching Authority for PCT/EP2018/066165 dated Sep. 28, 2018.

*Primary Examiner* — Patrick C Williams
(74) *Attorney, Agent, or Firm* — Millen White Zelano & Branigan, PC; Brion P. Heaney

(57) ABSTRACT

A gas cylinder monitoring system comprising a gas cylinder for receiving and distributing gas. A flow control valve is associated with the gas cylinder and operable to allow or prevent the flow of gas from the cylinder. A monitor is provided for monitoring a signal from an input device associated with the flow control valve. The monitor has an environmental parameter sensor for detecting the presence or absence of a selected environmental parameter in the vicinity of the cylinder. The environmental parameter sensor is connected to the monitor for transmitting an environmental status signal thereto. A removable cover is provided for covering both the flow control valve and the environmental parameter sensor such as to only allow access to the flow control valve when the cover is removed. A transmitter is also provided for transmitting a signal, obtained by the monitor from the input device, to a receiver.

17 Claims, 4 Drawing Sheets

(51) Int. Cl.
 *F17C 13/06* (2006.01)
 *G01N 33/00* (2006.01)
 *G01V 8/10* (2006.01)
(52) U.S. Cl.
 CPC ........... *G01N 33/0036* (2013.01); *G01V 8/10*
 (2013.01); *F17C 2201/0109* (2013.01); *F17C 2205/0308* (2013.01); *F17C 2205/0311* (2013.01); *F17C 2205/0329* (2013.01); *F17C 2205/0394* (2013.01); *F17C 2250/034* (2013.01); *F17C 2250/0478* (2013.01); *F17C 2270/02* (2013.01)
(58) Field of Classification Search
 CPC ........ F17C 2201/056; F17C 2205/0308; F17C 2205/0311; F17C 2205/0329; F17C 2205/0394; F17C 2205/0165; F17C 2250/034; F17C 2250/0478; F17C 2270/02; F16J 13/24; G01N 33/0036; G01V 8/10
 See application file for complete search history.

(56) References Cited

U.S. PATENT DOCUMENTS

| | | |
|---|---|---|
| 2009/0040049 A1 | 2/2009 | Delecourt et al. |
| 2011/0154868 A1 | 6/2011 | Eizen et al. |
| 2015/0041354 A1 | 2/2015 | Mitchell et al. |
| 2016/0245426 A1 | 8/2016 | Fowler et al. |
| 2017/0122497 A1 | 5/2017 | Bernard |
| 2018/0028769 A1* | 2/2018 | Obenchain ........ A61M 16/0051 |

* cited by examiner

GAS CYLINDER MONITORING SYSTEM

The present invention relates to a gas cylinder monitoring system and relates particularly but not exclusively, to a gas cylinder monitoring system using gas cylinders for supplying clinical gasses such as, for example, oxygen, argon, nitrous oxide, xenon, nitric oxide, helium and mixtures thereof to patients, and for supplying industrial gases such as oxygen, nitrogen and argon and mixtures thereof where it is desirable to know if use of the cylinder has commenced or not.

It is known to supply gas cylinders into a process including filling, transporting, storing and using before having the cylinders returned to the supplier for re-filling and then re-circulation within the process. Cylinders are often placed in storage for long periods of time or deployed from storage but remain unused and effective inventory management is sometimes difficult to achieve without significant and expensive manual checking of stock and the use status of that stock.

It is also known to supply cylinder systems with gauges displaying the pressure of gas remaining, but human intervention is normally required to retrieve the information and some users may find it difficult to interpret the information supplied and may make incorrect determinations of important data such as the total time of gas supply remaining. Still further, it is often very difficult to locate cylinder systems which may be past their use-by date or which may be obsolete or inappropriate for a location. Some cylinders may remain in storage or deployed but unused for prolonged periods of time and may pass their use by date before their contents have been accessed or completely used.

It will be appreciated that returning unused or partially used cylinders to the supplier is wasteful of time and gas and creates an administrative and technical burden on the staff and equipment at the storage or user locations.

It is an object of the present invention to reduce and possibly eliminate the above-mentioned problems by providing a system which is able to determine if and when a cylinder has been placed into potential use such as to allow staff to more easily manage inventory and gas usage.

Accordingly, the present invention provides a gas cylinder monitoring system comprising: a gas cylinder, for receiving and distributing gas contained therein; a flow control valve, associated with the gas cylinder operable to allow or prevent the flow of gas from said cylinder; a monitor, for monitoring a signal from an input device; and an input device associated with said flow control valve comprising an environmental parameter sensor for detecting the presence or absence of an environmental parameter in the vicinity of the cylinder and being operably connected to the monitor for transmitting an environmental status signal thereto and a removable cover covering both the flow control valve and the environmental parameter sensor such as to only allow access to the flow control valve upon removal of the cover; and a transmitter for transmitting a signal to a receiver obtained by the monitor from the input device.

In a simplified arrangement, said aid transmitter is operable to transmit a signal S indicating one or more of the covered or uncovered status of the environmental parameter sensor.

In a preferred arrangement, the input device may comprise a light sensor for detecting the presence or absence of light. Alternatively, said input device may comprise a humidity sensor for detecting the level of humidity in the air adjacent the input device. Still further, said sensor may comprise a micro-switch connected to the removable cover.

In one arrangement, said removable cover comprises a shrink-wrapped cover extending over one or other but preferably both the flow control valve and the environmental parameter sensor. Removal of the cover to access the flow control valve will cause light or humidity to be received by the sensor.

Advantageously, said transmitter is operable to periodically transmit a signal indicating the covered or uncovered status of the environmental parameter sensor. Such an arrangement will allow the status and location of the cylinder to be transmitted back to a central system and, thus, may avoid human involvement in cylinder inventory management.

Preferably, said transmitter is operable to transmit a signal only upon the uncovering of said environmental parameter sensor. Such an arrangement will save battery life but the absence of a signal will also indicate the cylinder has yet to be placed in service.

The transmitter may comprise one or more of: a Radio Frequency Identification (RFID); an Audio Transmitter; a Wireless Transmitter (WT); or a Bluetooth (BT) device.

The gas cylinder monitoring device may also include a receiver for receiving a signal transmitted from said transmitter. Such a receiver may be placed at a storage location or a use location.

When the gas cylinder monitoring device includes a receiver for receiving a signal transmitted from said transmitter, said further device may comprise one or more of: a Radio Frequency Identification Receiver (RFIDR); an Audio Receiver (AR); a Wireless Receiver (WR); or a Bluetooth Receiver (BR).

In one arrangement the device may include a receiver and said receiver is associated with a fixed location and said receiver is operably connected to a transmitter for transmitting a signal received by said receiver to a further receiver, such as to on-transmit received signals. Alternatively, said receiver may be associated with a movable location and said receiver may be operably connected to a transmitter for transmitting a signal received by said receiver to a further receiver, such as to on-transmit received signals.

Preferably, said a removable cover comprises a tamper evident cover.

Advantageously, said device further including a re-set button for causing the re-setting of the status of the environmental parameter sensor.

In a particularly convenient arrangement, said cylinder may include a casing surrounding said flow control valve and said environmental parameter sensor may be mounted on said casing.

The present invention will now be described by way of example only with reference to the accompanying drawings, in which.

Figure 1:
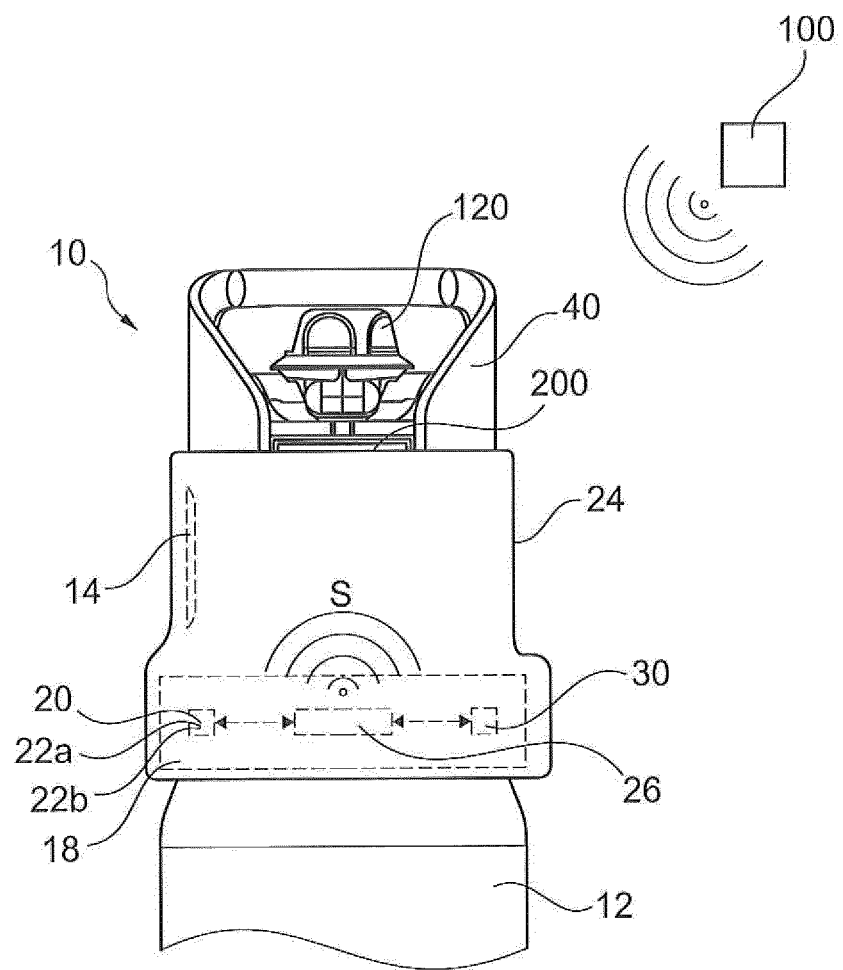
FIG. 1 is a front elevation of a gas cylinder incorporating a system according to an aspect of the present invention and illustrating the arrangement with the cover in place.

Referring now to the drawings in general but particularly to FIG. 1, a gas cylinder monitoring system 10 includes a gas cylinder 12 for receiving and distributing a gas, an outlet valve 14 and a monitor 18 operably connected to an input device 20 for monitoring a signal from said input device 20. The input device 20 is operable to monitor one or more environmental parameters in the vicinity of the cylinder such as, for example, light or humidity or both thereof. A transmitter 26 is operably connected to the monitor 18 for transmitting a signal S from the monitor 18 to a receiver 100 as and when required. A removable cover 24 is provided over both outlet valve 14 and the input device 20 such as to isolate each from the environment until the cylinder is required. It will be appreciated that, before a user can operate the outlet valve 14, the removable cover 24 must be removed and this will expose the input device 20 to the local environment and, thus, allow the input device 20 to detect the existence of a monitorable environmental parameter. It is the detection of this parameter or a change in state of detection that is used by the present invention to monitor when the cylinder 12 is activated for potential use. Clearly, in the absence of the input device 20 being uncovered the cylinder 12 will not be in use and, hence, the absence of a detected parameter may also be used to create a status signal which may be relayed or further transmitted as discussed in detail later herein.

The input device 20 may comprise a light sensor 22a for the detection of light. When using such a sensor it will be necessary to provide the removable cover 24 in the form of a light isolating cover so as to prevent, or at least restrict, light being transmitted to the device 20 when covered. Alternatively, the input sensor 20 may comprise a humidity sensor 22b for detecting the level or existence of humidity in the air adjacent the input device 20.

A reset button 30 may be provided and operably connected to the monitor 18 and input device 20 if needed so as to allow for the re-setting of the status signal or monitoring system itself 10. Such a re-set button 30 will be of use if the cover 24 has been removed and then replaced, such as may occur when the cylinder 12 has been put into use and then returned to store or to the supplier.

Figure 2:
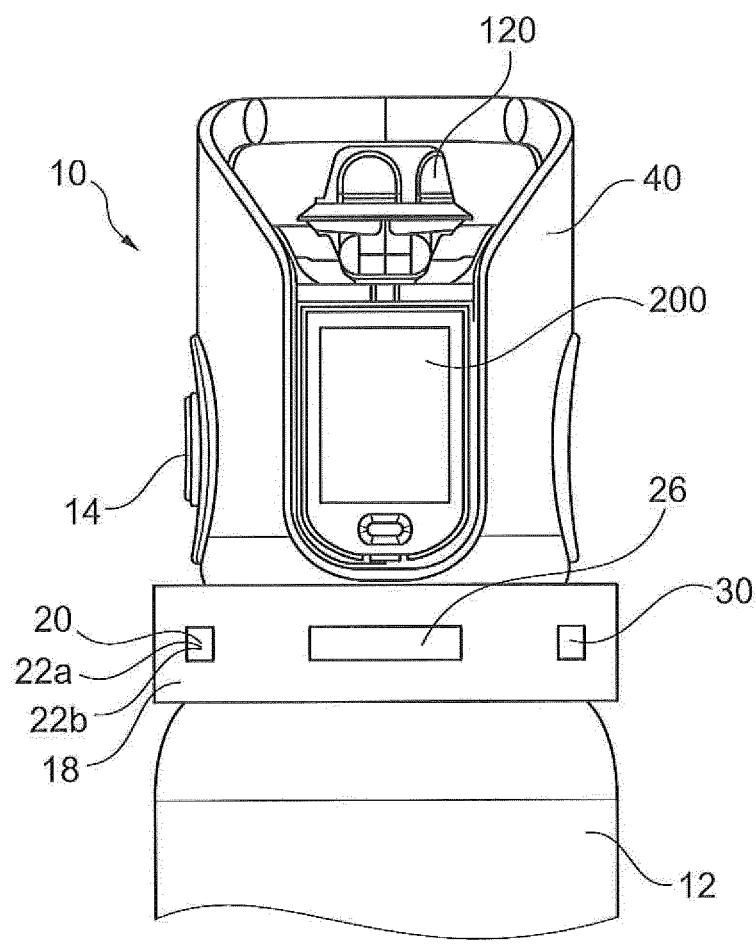
FIG. 2 is a front elevation of the arrangement of FIG. 1 with the cover removed.
Figure 3:
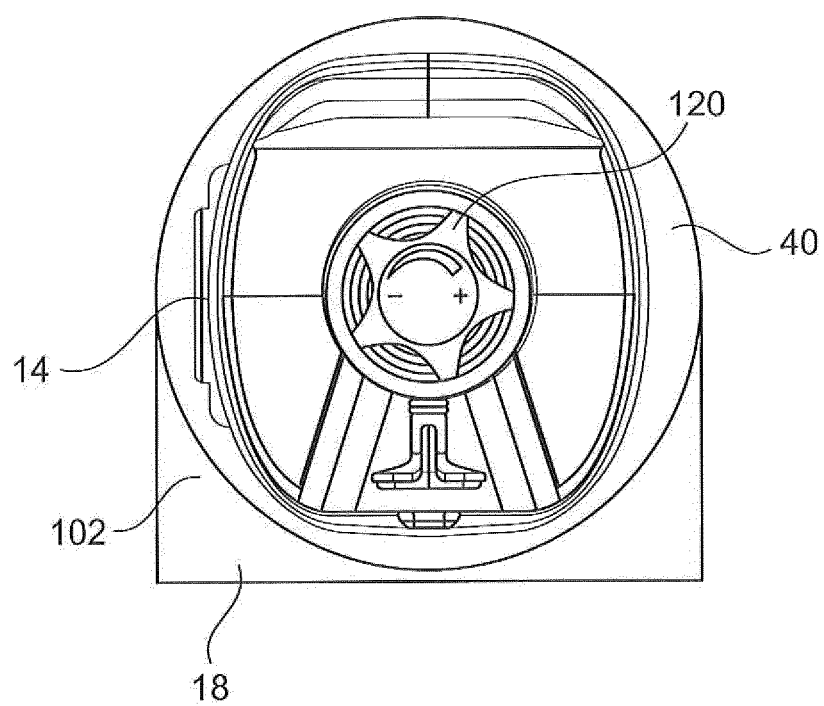
FIG. 3 is a plan view of the arrangement of FIG. 1 showing the cover in position.
Figure 4:
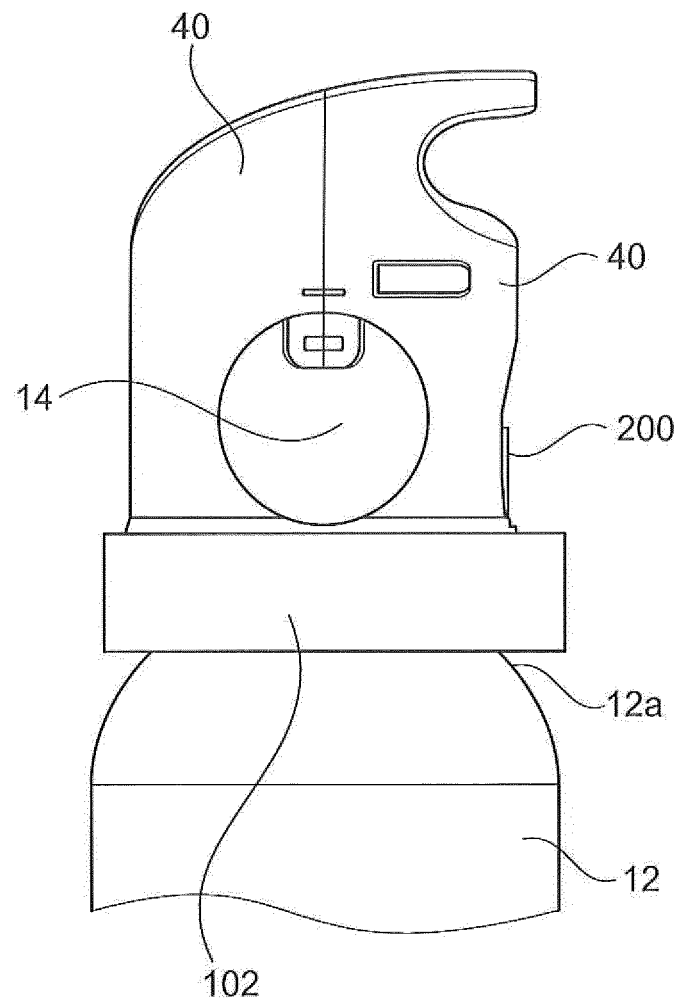
FIG. 4 is a side view of the arrangement of FIG. 2 with the cover removed.

Mounting of the monitoring system 10 relative to the cylinder 12 and valve 14 may be achieved in any one of a number of ways. One possible way would be to provide the monitoring system 10 in the form of a collar 102 which is positioned around the neck 12a of the gas cylinder 12 before the valve 14 is connected to the cylinder 12. Such an arrangement would allow the valve 14 to prevent the removal of the monitoring system 10 unless the valve itself was removed. This arrangement would also allow the monitoring system 10 to be retro-fitted to existing cylinders 12 and valves 14 without further modification. Alternatively, if the cylinder and valve arrangement is provided with an outer casing 40 such as that shown exposed in FIGS. 2 and 3, it will be possible to incorporate the monitoring system 10 into such a casing 40 or an extension thereof, the latter of which is shown in FIG. 2. It will be appreciated that when a casing 40 is provided, one or more or all of the input device 20, monitor 18 and transmitter 26 may also be mounted on or within the casing 40 or extension thereof. Indeed, when so mounted they may individually or collectively be connected to any further computing or display device 200 that may be provided in association with the valve 14 or cylinder 12.

It will be appreciated that any one of a number of removable covers 24 may be provided so long as they provide the function of covering sensor 20 from the environment and also isolating the outlet valve 14 from any potential operative until the cover 24 is removed. A particularly appropriate removable cover would be one which is tamper evident cover such as one having a breakable seal or one which requires the destruction thereof in order to remove the seal.

Simple examples include shrink wrapped plastic film which is shrunk wrapped around the casing 40 such as to cover both the sensor 20 and the valve 14. If the plastic were impervious to light or at least restricted the amount of light that could be transmitted to the sensor 20 then this would perform the function of isolating a light sensitive sensor 22a from any light that may be in the location or vicinity of the cylinder 14. If the plastic was impervious to humidity then the plastic could perform the function of isolating a humidity sensitive sensor 22b from the local environment. Alternatively, when the sensor 20 comprises a micro-switch, the switch can be physically connected to the removable cover such as to allow the switch to be activated upon removal of the cover and the switch could then be used to initiate activation of a warning or transmit the required signal.

The transmitter may be operated in any one of a number of ways including but not limited to the following:
a) Periodically transmitting a signal indicative of the covered or uncovered status of the sensor 20;
b) To transmit a single signal indicative of the uncovered status of the sensor 20 upon uncovering of the sensor 20;
c) To periodically transmit a signal indicative of the uncovered status of the sensor 20 after said sensor is uncovered.

It will be appreciated that once the removable cover 24 is removed the operator can open the outlet valve 14 and cause the flow of gas and, hence, knowing the cover has been removed provides a good indication that the cylinder 12 has been pressed into service and the inventory management system can be updated accordingly, either manually or automatically via the signal S transmitted from transmitter 26. The cylinder 12 is normally provided with a flow regulator valve 120 of higher controllability and accuracy of flow downstream from the outlet valve 14 which is only able to cause the controlled delivery of gas upon the opening of the outlet valve 14 itself.

It will also be appreciated that the transmitter itself 26 may comprise any one of a number of transmitters of the type well known in the art and, therefore, not described herein other than to recite the options such as: a Radio Frequency Identification (RFID) device; an Audio Transmitter; a Wireless Transmitter (WT); or a Bluetooth (BT) device. Whatever transmitter that is provided, it is configured to transmit a signal S to a receiver 100 which may itself be configured as a transceiver such as to allow the signal to be onward transmitted to a further receiver 200. Such an arrangement would allow the status signal S to be transmitted to a further location where it may be used for inventory monitoring purposes. The further device 200 may also comprise one or other of: a Radio Frequency Identification (RFID) device; an Audio Transmitter; a Wireless Transmitter (WT); or a Bluetooth (BT) device.

It will also be appreciated that the receiver 100 may be at a fixed location such as in a store room or in an operating theatre or on a ward and that by transmitting signal S thereto the location of the cylinder 14 may also be determined and transmitted. Receiver 100 might be in a movable location such as in an ambulance (not shown) such as to allow for the location of the cylinder off-site and, potentially, also to allow for the location of the ambulance relative to the hospital. In either of the fixed or movable locations, transmitter 100 may be configured as a transceiver such as to both receive and then onward transmit signals from the transmitter 26.

The above-described monitoring system will allow the supplier to track the location of cylinders 14 when in use or when in store and may be used to locate cylinders when in need of replacement or re-filling due to expiry of use-by dates or low contents or inappropriate location of cylinders in hazardous locations or where multiple cylinders are in the same location when only one is required in said location. The system will also allow for the convenient location of cylinders without significant manual input and for stock-control and possible stock re-allocation on a "just in time" basis, thus reducing stock whilst ensuring continuity of supply.

Whilst the cylinders could be used for any one of several gasses it has been found that the monitoring system is of particular importance for gases such as clinical gasses including, for example, oxygen, argon, nitrous oxide, xenon, nitric oxide, helium and mixtures thereof to patients, and for supplying industrial gases such as oxygen, nitrogen and argon and mixtures thereof, as the inventory management of such gasses is important to the safe use thereof.

The invention claimed is:

1. A gas cylinder monitoring system (10) comprising:
   a) a gas cylinder (12) for receiving and distributing gas contained therein,
   b) a flow control valve (14) associated with the gas cylinder (12) operable to allow or prevent the flow of gas from said cylinder (12);
   c) a monitor (18) for monitoring a signal from an input device (20) associated with said flow control valve;
   d) said input device (20) comprising an environmental parameter sensor (22) for detecting the presence or absence of an environmental parameter in the vicinity of the cylinder (12) and being operably connected to the monitor (18) for transmitting an environmental status signal thereto;
   e) a removable cover (24) covering the flow control valve (14), the monitor (18), and the environmental parameter sensor (22) so as to only allow access to the flow control valve (14) upon removal of the cover (24); and
   f) a receiver and a transmitter (26),
   wherein said transmitter is operable to transmit a signal obtained by the monitor (18), from the input device, to said receiver (100), and wherein the signal is indicative of one or more of the covered or uncovered status of the environmental parameter sensor.

2. A gas cylinder monitoring system (10) as claimed in claim 1, wherein said environmental parameter sensor (22) is a light sensor (22-a) for detecting the presence or absence of light.

3. A gas cylinder monitoring system (10) as claimed in claim 1, wherein said environmental parameter sensor (22) is a humidity sensor (22-b) for detecting the level of humidity in the air adjacent the input device (20).

4. A gas cylinder monitoring system (10) as claimed in claim 1, wherein said removable cover (24) comprises a shrink-wrapped cover extending over both the flow control valve (14) and the environmental parameter sensor (22).

5. A gas cylinder monitoring system as claimed in claim 1, wherein said transmitter (26) is operable to periodically transmit the signal indicating the covered or uncovered status of the environmental parameter sensor (22).

6. A gas cylinder monitoring system (10) as claimed in claim 1, wherein said transmitter (26) is operable to transmit the signal only upon the uncovering of said environmental parameter sensor.

7. A gas cylinder monitoring (10) as claimed in claim 1, wherein said transmitter (26) comprises one or more of: a Radio Frequency Identification (RFID); an Audio Transmitter; or a Wireless Transmitter (WT).

8. A gas cylinder monitoring device (10) as claimed in claim 1, wherein said receiver comprises one or more of: a Radio Frequency Identification Receiver (RFIDR); an Audio Receiver (AR); or a Wireless Receiver (WR).

9. A gas cylinder monitoring device (10) as claimed in claim 1, wherein said receiver (100) is associated with a fixed location and wherein said receiver (100) is operably connected to a further transmitter (120) for transmitting the signal received by said receiver (100) to a further receiver.

10. A gas cylinder monitoring device (10) as claimed in claim 1, wherein said receiver (100) is associated with a movable location and wherein said receiver (100) is operably connected to a further transmitter (120) for transmitting the signal received by said receiver (100) to a further receiver (200).

11. A gas cylinder monitoring device (10) as claimed in claim 1, wherein said removable cover (24) comprises a tamper evident cover.

12. A gas cylinder monitoring device (10) as claimed in claim 1, further comprising a re-set button for causing re-setting of the status of the environmental parameter sensor (22).

13. A gas cylinder monitoring device (10) as claimed in claim 1, wherein said cylinder (14) includes a casing (40) surrounding said flow control valve (14) and wherein said environmental parameter sensor (22) is mounted on said casing (40).

14. A gas cylinder monitoring system (10) as claimed in claim 1, wherein said input device (20) comprises a switch connected to the removable cover (24) for detecting the presence or absence of the cover (24).

15. A gas cylinder monitoring system (10) as claimed in claim 1, wherein said transmitter is operable to transmit the signal only when said environmental parameter sensor (22) is uncovered by removal of said removable cover (24).

16. A gas cylinder monitoring system (10) as claimed in claim 1, wherein said monitoring system (10) is mounted to said gas cylinder (12) by a collar (102) positioned around a neck of (12a) of said gas cylinder (12) such that said monitoring system (10) cannot be removed unless flow control valve (14) is removed.

17. A gas cylinder monitoring system (10) as claimed in claim 1, wherein said transmitter is operable to:
   a) periodically transmit the signal indicative of the covered or uncovered status of the sensor;
   b) transmit the signal in the form of a single signal indicative of the uncovered status of the sensor upon uncovering of the sensor; or
   c) periodically transmit the signal indicative of the uncovered status of the sensor after said sensor is uncovered.

* * * * *